(12) United States Patent
Harvey

(10) Patent No.: US 6,423,488 B1
(45) Date of Patent: Jul. 23, 2002

(54) HIGH THROUGHPUT SCREENING ASSAY FOR DETECTING A DNA SEQUENCE

(75) Inventor: Alex J. Harvey, Athens, GA (US)

(73) Assignee: AviGenics, Inc, Athens, GA (US)

( * ) Notice: Subject to any disclaimer, the term of this patent is extended or adjusted under 35 U.S.C. 154(b) by 0 days.

(21) Appl. No.: 09/760,048

(22) Filed: Jan. 13, 2001

Related U.S. Application Data

(60) Provisional application No. 60/176,255, filed on Jan. 15, 2000.

(51) Int. Cl.[7] .......................... C07H 21/02; C12Q 1/68; C12Q 1/70; A21C 11/16
(52) U.S. Cl. .............................. 435/5; 435/6; 536/23.1; 425/288.1
(58) Field of Search ........................ 435/5, 6; 536/23.1; 425/288.1

(56) References Cited

PUBLICATIONS

J. Sambrook et al., Molecular Cloning.*
"DNA Extraction from Nucleated Red Blood Cells"; J.F. Medrano, E. Aasen, L. Sharrow, BioTechnques 8 (1), 43, 1990.
"Detection of specific polymerase chain reaction product by ulilizing the 5'→3'exonuclease activity of *Thermus acquaticus* DNA polymerase"; P.M. Holland, R.D. Abramson, R. Watson, D.H. Gelfand, Proc. Natl. Acad. Sci. USA 88, 7260–7280, 1991.
"Genomic DNA Microextraction: A Method to Screen Numerous Samples"; R. Ramirez–Solis, J. Rvera–Perez J.D. Wallace, M. Wims, H. Zheng, A. Bradlely, Analytical Biochemistry 201, 331–335, 1992.
"Isolation of Genomic DNA from Avian Whole Blood"; J.N. Petitte, A.E. Kegelmeyer, M.J. Kulik, BioTechniques 17 (4), 664, Jul. 14, 1994.

"Microplate DNA Preparation , PCR Screening and Cell Freezing for Gene Targeting in Embryonic Stem Cells"; G.B. Udy, M.J. Evans, BioTechniques 17 (5), 887–894, Aug. 16, 1994.
"Germline transmission of exogenous genes in chickens using helper–free ecotropic avian leukosis virus–based vectors", P. Thoraval, M. Afanassieff, F.L. Cosset, F. Lasserre, G. Verdier, F. Coudert, G. Dambrine, Transgenic Research 4, 369–376, 1995.
"Continuous Fluorescence Monitoring of Rapid Cycle DNA Amplification"; C.T. Wittwer, M.G. Herrmann, A.A. Moss, R.P. Rasmussen, BioTechniques 22(1), 130–138, Jan. 1997.
"Improved Protocol for Using Avian, Red Blood Cells as Substrates for the Polymerase Chain Reaction"D. Bercovich, Y. Plotsky, Y. Gruenbaum, BioTechniques 26 (6), 1080–1082, Jun. 1999.

* cited by examiner

*Primary Examiner*—Andrew Wang
*Assistant Examiner*—Karen A. Lacourciere
(74) *Attorney, Agent, or Firm*—Judy Jarecki-Black

(57) ABSTRACT

Genetic modification or selection of avians requires that large numbers of birds be genetically analyzed for sequences of interest. Typically, DNA is extracted on an individual basis from samples taken from the birds. Current methods of DNA extraction extract the DNA from blood or other tissues using tedious and time-consuming procedures. The present invention provides a high throughput screening assay for detecting a genetic sequence in multiple samples. The assay further provides a DNA extraction method that allows DNA to be extracted rapidly from multiple avian samples, such as red blood cells. The extraction method is extremely reliable and does not require that each sample be quantitated post-extraction. The extracted DNA can be used for a variety of genetic assays, including a high throughput screening assay to identify insertion of a transgene. The present invention is particularly useful for extracting DNA from nucleated RBCs. Therefore, the method can be applied towards genetic analysis of avians, fish, reptiles and amphibians.

16 Claims, 8 Drawing Sheets

Figure 1. High throughput extraction of avian blood DNA.

```
                  Neo for-1
     ─────────────────────▶
     TGGATTGCAC GCAGGTTCTC CGGCCGCTTG GGTGGAGAGG CTATTCGGCT
     ACCTAACGTG CGTCCAAGAG GCCGGCGAAC CCACCTCTCC GATAAGCCGA
                          ◥───────────────────◤   ◥─────────
                              Neo probe              Neo rev-1

ATGACTGGGC AC
     TACTGACCCG TG
     ──────────────
     Neo rev-1(cont.)
```

Figure 6

HIGH THROUGHPUT SCREENING ASSAY FOR DETECTING A DNA SEQUENCE

The present application claims the benefit of priority from a provisional application filed Jan. 15, 2000 and having U.S. Ser. No. 60/176,255.

FIELD OF THE INVENTION

The present invention relates generally to a screening assay and, more specifically, to a high-throughput screening assay useful for detecting the presence of a foreign DNA sequence in a sample. The present invention further includes a high throughput extraction method for extracting DNA from nucleated cells, particularly red blood cells.

BACKGROUND OF THE INVENTION

The present invention provides a high throughput screening assay useful for detecting the presence of an exogenous DNA sequence in a sample. The method of the present invention further includes a high throughput DNA extraction method useful for extracting DNA from avian blood for subsequent use in a screening assay as, for example, an assay to detect the insertion of foreign DNA in the genome of a recipient.

The publications cited herein to clarify the background of the invention and in particular, materials cited to provide additional details regarding the practice of the invention, are incorporated herein by reference, and for convenience are cited in the following text.

Transgenesis is the ability to introduce foreign or exogenous DNA into the genome of a recipient, as for example, into a sheep, a cow or even a chicken. The ability to alter the genome of an animal immediately suggests a number of commercial applications, including the production of an animal able to express an exogenous protein in a form that is harvested easily.

The main obstacle to avian transgenesis is the low efficiency of introduction of foreign DNA into the chicken genome. The insertion of foreign DNA into the chicken genome using procedures that have worked for other animals is a difficult task and attempts at such have been mostly unsuccessful, partly due to the unique physiology of the chicken (Love et al., Transgenic birds by DNA microinjection, *Biotechnology* 12: 60–63, 1994; Naito et al., Introduction of exogenous DNA into somatic and germ cells of chickens by microinjection into the germinal disc of fertilized ova, *Mol Reprod Dev* 37: 167–171, 1994).

Through the use of retroviruses, a number of research groups have successfully introduced foreign DNA into the chicken genome at acceptable but low efficiencies (Bosselman et al., Germline transmission of exogenous genes in the chicken, *Science* 243: 533–5, 1989; Petropoulos, et al., Appropriate in vivo expression of a muscle-specific promoter by using avian retroviral vectors for gene transfer [corrected] [published erratum appears in *J Virol* 66: 5175, 1992] *J Virol* 66: 3391–7, 1992; Thoraval. et al., Germline transmission of exogenous genes in chickens using helper-free ecotropic avian leukosis virus-based vectors, *Transgenic Res* 4: 369–377, 1995). The retroviral vectors used have been engineered such that they will not result in the replication and spread of any new retroviruses. This allows production of transgenic chickens that are free of any retrovirus. However, because the retroviral vectors cannot propagate in the chicken, the transgene is not transmitted from cell to cell. Retroviral vectors are typically injected into the embryo of a freshly laid egg through a small window in the egg shell. Approximately 1% of the embryonic cells are transduced, such that one copy of the transgene is inserted into the cell's DNA. After sexual maturity and meiosis, 0.5% of sperm or oocytes carry the transgene. In order to obtain one transgenic bird, at least 200 chicks have to be screened. It is often desirable to obtain several transgenic chicks because different chromosomal insertions can lead to different levels of transgene expression. Thus, it is necessary to breed and screen hundreds to thousands of chicks, necessitating a method for high throughput genetic screening for detecting the desired genetic sequence.

Random chromosomal insertion of transgenes via non-retroviral methods has become the mainstay of transgenics in some domesticated animals including pigs, sheep, goats and cows. The primary method to introduce the transgene is the injection of linearized DNA containing the desired transgene into the pronucleus of a zygote. Up to 20% of $G_o$ offspring contain the transgene. The relative high efficiency of transgenesis offsets the high technical costs incurred during the procedure. Transgenes have been inserted into goats, for instance, that direct the expression of pharmaceuticals in mammary glands for subsequent secretion into milk (Ebert, et al., Transgenic production of a variant of human tissue-type plasminogen activator in goat milk: generation of transgenic goats and analysis of expression, *Biotechnology* 9: 835–8, 1991).

In chickens, injection of the zygote germinal disk has been accomplished but with limited success, in part due to additional complications associated with unique aspects of chicken physiology and embryogenesis (Love et al., 1994; Naito et al., 1994). One lab has successfully produced several transgenic chickens, which have incorporated the injected DNA into their chromosomes and passed the transgene on to offspring. Another lab attempted to reproduce the technique but failed. Zygote injections in chickens are difficult because the nucleus is very small and is about 50 microns below the yolk membrane. Thus, the DNA must be injected into the cytoplasm. As in mice, cytoplasmic injection of DNA results in inefficient incorporation of the transgene into the chromosomes. Chickens must be sacrificed in order to remove the zygote and each chicken yields only one zygote.

An important technical breakthrough was pioneered by Gibbins, Etches, and their colleagues at the University of Guelph by using blastodermal cells (BDCs) collected from embryonic stage X embryos at oviposition, e.g., the time when the egg is laid (Brazolot et al., Efficient transfection of chicken cells by lipofection, and introduction of transfected blastodermal cells into the embryo, *Mol Reprod Dev* 30: 304–12. 1991; Fraser, et al., Efficient incorporation of transfected blastodermal cells into chimeric chicken embryos, *Int J Dev Biol* 37: 381–5, 1993). Coupled with recent progress in the culturing of BDCs, which can still reconstitute the germline, the method theoretically enables random transgene addition via nonhomologous recombination as well as targeted gene engineering via homologous recombination.

At stage X, the embryonic blastoderm consists of 40,000 to 60,000 cells organized as a sheet (area pellucida) surrounded by the area opaca; it harbors presumptive primordial germ cells (PGCs) that have not yet differentiated into migrating PGCs. Dispersed BDCs can be transfected with an appropriate transgene and introduced into the subgerminal cavity of y-irradiated, recipient stage X embryos. Irradiation may selectively destroy presumptive PGCs and retard recipient embryo growth allowing injected cells additional time to populate the recipient blastoderm. Using genetic markers for feather color (black for Barred Rock and white for White Leghorn), Etches, Gibbins and their colleagues were able to show that, of injected embryos surviving to hatch, 50% or greater of these were somatic chimeras of which nearly half were also germline mosaics (Petitte, et al., Production of somatic and germine chimeras in the chicken by transfer of early blastodermal cells, *Development* 108: 185–9, 1990).

Gibbins and her colleagues have determined that random gene addition occurs in in vitro cultured BDCs in 1 out of every 300 transfected cells (Gibbins and Leu, personal communication). They did not determine whether BDCs with random gene additions can be re-introduced into stage X embryos to produce germline $G_o$ chimeras. Therefore, the actual efficiency of transgenesis has not yet been determined.

Gene targeting, the ability to specifically modify a specific gene, is a much sought-after technology in a variety of species, including chickens, because such modifications will result in very predictable transgene expression and function. Gene targeting has been successfully accomplished in mice because mouse embryonic stem (ES) cells can be cultured in vitro for long periods of time and still contribute to the germline (Mountford et al., Dicistronic targeting constructs: reporters and modifiers of mammalian gene expression, *Proc Natl Acad Sci USA* 91: 4303–7, 1994). The long-term culture of mouse ES cells allows the researcher to select for and expand colonies of cells transfected with the targeting vector that have the transgene inserted into the proper site. Similar to the use of the feather color alleles in chimeric birds, coat color of different breeds of mice are used to track the donor cells in offspring. The difficulty in applying the mouse ES cell technology to other species is that it has been impossible to isolate ES cells of other species. While cells resembling ES cells have been isolated from goats and pigs and cultured in vitro, these cells are not able to contribute to recipient embryos after long-term culture. Nuclear transfer technology offers an alternative to the use of ES cells and it is probable that gene targeting in animals will, in the future, be implemented via nuclear transfer. Presently, however, nuclear transfer is very inefficient and expensive, making its implementation a slow process.

Recent advances in the in vitro short-term culture of chicken blastodermal cells, combined with the unique physiology of avian reproduction, indicate that gene targeting is possible in chickens. The division rate of stage X BDCs can be maintained in vitro at one division every 8–10 hours for 4–8 days using culture conditions developed by the Ivarie laboratory (University of Georgia, Athens, Ga.) and AviGenics, Inc. (Athens, Ga.) (Speksnijder and Baugh, unpublished data). The ability to propogate BDCs in vitro at this rate, while maintaining totipotency, will allow for the rapid expansion of cell colonies containing the desired genetic modification. This, combined with the fact that large numbers of BDCs (40,000 to 60,000 cells/egg) can easily be isolated from freshly laid chicken eggs, makes it feasible to screen large numbers of transfected BDC colonies for those having a desired gene of interest.

Currently, BDCs can only be cultured for 4 to 8 days before they lose the ability to contribute to germ tissues in the recipient embryo (Speksnijder and Baugh, unpublished data). Therefore, it is likely that BDCs carrying the desired genetic modification can only be enriched to perhaps 0.1 to 10% of the total number of donor cells. While sufficient to enable gene targeting, the rate of transmission of the desired genetic modification from chimeric founder animals (those that were directly derived from injection of donor BDCs into recipient embryos) to their offspring will be low. Hundreds to thousands of offspring will have to be screened, again necessitating a method for high throughput genetic screening for detecting a desired sequence.

The enrichment of BDCs for desired genetic modifications can be applied to transgenesis projects involving random insertion of a gene into the avian genome, as well as modification of a specific gene. Therefore, a method for high throughput genetic screening will have broad applications in the fast-growing field of avian transgenesis.

To determine if an organism contains a novel or new gene, DNA is extracted from a tissue sample (blood, skin, sperm) and is subjected to an assay that will detect the gene. The method of choice was the Southern assay, which is extremely sensitive and reliable (Southern, E. M., Detection of specific sequences among DNA fragments separated by gel electrophoresis, *J Mol Biol* 98, 503–17, 1975). However, the Southern assay is very labor intensive and time consuming.

The Southern assay was replaced by the polymerase chain reaction (PCR) method (Mullis et al., Specific enzymatic amplification of DNA in vitro: the polymerase chain reaction. *Cold Spring Harbor Symp Quant Biol* 51 (Pt 1): 263–73, 1986), which is a more sensitive and rapid assay.

Recently developed techniques, such as the TAQMAN sequence detection system (Applied Biosystems, Foster City, Calif.) allow hundreds of samples to be analyzed in hours without requiring a time-consuming gel electrophoresis step (Heid et al. Real time quantitative PCR, *Genome Res* 6: 986–94, 1996). During a TAQMAN reaction run, which is setup like a PCR reaction, a fluorogenic probe consisting of an oligonucleotide with both a reporter and a quencher fluorescent dye attached, anneals specifically between the forward and reverse primers. The probe and primers are complementary to the sequence of the desired transgene. When the probe is cleaved by the 5' nuclease activity of Taq DNA polymerase, the reporter dye is separated from the quencher dye and a sequence-specific signal is generated. With each cycle, additional reporter dye molecules are cleaved from their respective probes, and the fluorescence intensity is monitored during the PCR. Samples are analyzed in 96-well plates and, at the end of a run, it is obvious which samples contain the desired sequence.

While high throughput methods for sequence detection are available, no comparable methods exist for the extraction of DNA useful in a high throughput assay for sequence detection. Rather, existing DNA extraction methods are still labor intensive and time consuming. The majority of extraction methods require the DNA samples to be treated in individual tubes. Samples are subjected to a number of steps, including proteinase digestion, extraction with organic solvents, and precipitation. The extraction step is particularly problematic because of the awkwardness of manipulation of the solution phases. Salting out has been used as an alternative for extraction of unwanted proteins, but this method requires multiple centrifugations and tube transfers. Kits are available which avoid the extraction steps by using DNA binding resins and allow for the processing of 96 samples at a time. However, the resins are not reusable, and their use can result in poor yield and inconsistent DNA quality. In addition, these kits are not cost-effective, costing up to $3.00 per sample processed for extraction.

Existing methods for extracting DNA extraction from multiple samples of avian tissue are labor intensive and tedious. Avian blood, like all non-mammalian vertebrates, has a special quality in that the erythrocytes are nucleated (Rowley and Ratcliffe, Vertebrate blood cells, Cambridge University Press, Cambridge, N.Y., 1988). The presence of nucleated cells allows one to extract a large amount of DNA from a very small amount of blood. But existing DNA extraction techniques have not taken advantage of this aspect of avian blood. Grimberq. et al. developed a method in which the plasma membrane, but not the nuclear membrane, of red blood cells (RBCs) was lysed (Grimberg et al., A simple and efficient non-organic procedure for the isolation of genomic DNA from blood, *Nucleic Acids Res* 17: 8390, 1989). Subsequently, Petitte et al. augmented Grimberg's method by optimizing the initial lysis and spooling ethanol-precipitated DNA out on a glass rod, resulting in a more pure DNA preparation but requiring a more labor-intensive protocol (Petitte, et al., Isolation of genomic DNA from avian whole blood, *Biotechniques* 17: 664–6, 1994). Thoraval, et al. used a similar procedure, however, each sample was required to be treated individually (Thoraval et al., Germlne transmission of exogenous genes in chickens using helper-free ecotropic avian leukosis virus-based vectors, *Transgenic Res* 4: 369–377, 1995).

All of the aforementioned procedures possess similar disadvantages in that the each sample must be treated individually and the DNA extracted must be transferred between multiple tubes. In addition to being labor-intensive, these DNA extraction procedures increase both the possibility of contamination among samples and loss of DNA.

In order to target genes in mice, hundreds of mouse embryonic stem (ES) cell colonies have to be individually analyzed for the presence of the desired genetic modification. In order to facilitate DNA extraction from a large number of colonies, Ramirez-Solis et al. devised an ingenious method in which ES cells are lysed in 96-well plates (Ramirez-Solis et al., Genomic DNA microextraction: a method to screen numerous samples. *Anal Biochem* 201: 331–5, 1992). Using the method of Ramirez-Solis, et al., DNA is precipitated such that it sticks to the bottom of the microtiter well without centrifugation. This is due in part to the affinity of DNA for polystyrene, the major component of 96-well tissue culture plates. While the DNA is stuck to the plates, all the unwanted protein and salts can be removed by washing the wells multiple times with 70% ethanol. In this way, 96 samples can be processed simultaneously. Because the DNA is not transferred among tubes, the possibility of both sample loss and contamination is minimized.

Ramirez-Solis et al. attempted to isolate DNA from human blood samples using the above-described method, however the inefficiency of the procedure required processing a large volume of blood to obtain enough cells for efficient extraction. At least 0.3 ml, and most probably about 1.0 ml, of human blood is required per well to obtain enough DNA for efficient extraction, however the maximum capacity of each microtiter well is only about 0.25 ml. Thus, the method of Ramirez-Solis, et al. is not useful for the high throughput extraction of DNA from genomic blood.

Udy and Evans developed a 96-well plate method for DNA extraction from embryonic stem (ES) cells, similar to the method of Ramirez-Solis et al., but never applied their method to the extraction of DNA from blood (Udy and Evans, Microplate DNA preparation, PCR screening and cell freezing for gene targeting in embryonic stem cells, *Biotechniques* 17: 887–94,1994).

In view of the aforementioned deficiencies of the prior art, there is a need for a method providing for the rapid and easy extraction of DNA from a large number of blood samples without necessitating large sample volumes or labor intensive steps, or requiring the transfer of DNA between multiple tubes. Further, there is a need for a DNA extraction method that can be used in an high throughput assay to rapidly screen a large number of samples to detect a desired DNA sequence or transgene. Finally, there is a need for a high-throughput assay useful for detecting the presence of a desired genetic sequence in a large number of samples when the copy number is low, i.e., between about 5 to about 50 copies.

SUMMARY OF THE INVENTION

The present invention recognizes and addresses the above noted deficiencies and drawbacks of the prior art. The present invention provides a rapid method for extracting and preparing DNA for use in a subsequent high-throughput screening assay. The method of the present invention is especially useful for extracting DNA from avian blood for use in a high throughput screening assay as, for example, an assay to detect the insertion of foreign DNA in the genome of a recipient.

The present invention is also directed to an assay useful for rapidly screening a large number of nucleated blood samples to detect a desired genetic sequence. In one embodiment of the present invention, the nucleated blood samples may be avian blood such as, for example, from a chicken or turkey. The genetic sequence may be an endogenous DNA gene or a foreign sequence such as, for example, a transgene, or alternately, the genetic sequence may be a plasmid.

In one embodiment of the present invention, a nucleic acid is isolated from a nucleated blood sample, particularly an avian blood sample, by placing the sample in a microtiter well, lysing the cells to release the DNA, precipitating the nucleic acid within the well of the microtiter plate such that the nucleic acid is attached to the well, removing any extraneous material from the well by washing, and subjecting the isolated nucleic acid to a screening assay to detect a desired genetic sequence.

The present invention also provides a high throughput assay for detecting a desired sequence; the assay further comprising a sequence tag that permits a desired genetic sequence to be detected at low copy numbers even in the presence of interfering genomic DNA. In one embodiment, the high-throughput assay provides a sequence tag which permits a target plasmid to be detected in the presence of chicken genomic DNA at a level of from about 5 to about 50 copies.

BRIEF DESCRIPTION OF THE FIGURES

A full and enabling disclosure of the present invention, including the best mode thereof, to one of ordinary skill in the art, is set forth more particularly in the remainder of the specification, including reference to the accompanying Figures, in which:

FIG. 6 shows the nucleotide sequence of the sequence tag;

DETAILED DESCRIPTION OF THE PREFERRED EMBODIMENTS

Figure 1:
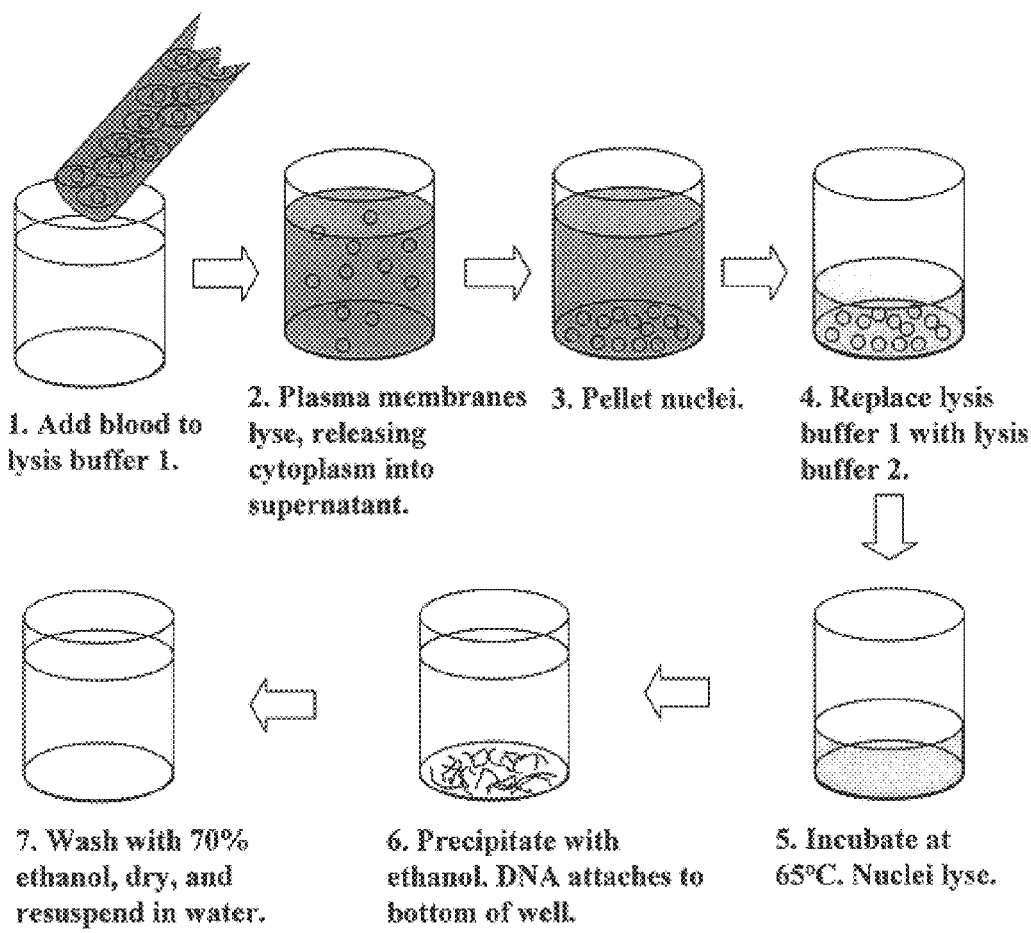
FIG. 1 is a schematic illustrating the method of the present invention.

Reference now will be made in detail to the presently preferred embodiments of the invention, one or more examples of which are illustrated in the accompanying drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used in another embodiment to yield a still further embodiment. It is intended that the present invention covers such modifications and variations as come within the scope of the appended claims and their equivalents.

The present invention is directed to a high-throughput assay useful for rapidly screening a large number of samples to detect a desired genetic sequence as, for example, a transgene or plasmid.

In one aspect of the present invention, a rapid method for extracting and preparing DNA for use in the high-throughput screening assay is provided. The method of the present invention is especially useful for extracting DNA from nucleated blood for use in a high throughput screening assay including, but not limited to, a polymerase chain reaction (PCR), ligase chain reaction (LCR), or other conventional DNA detection assay for the detection of genetic markers or foreign DNA in the genome of a recipient.

In one embodiment of the present invention, a high throughput method for extracting DNA from multiple samples of chicken blood is disclosed, as for example, from White Leghorn and Barred Rock chicks and fully mature birds. However, the method of the present invention can be used for the high throughput extraction of a DNA from any nucleated blood cell including, but not limited to, avian, fish, reptile and amphibian nucleated blood cells.

The present invention provides a high throughput method for extracting DNA from multiple blood samples containing nucleated blood cells without requiring the repositioning of the DNA into separate tubes or vessels during the extraction procedure. In one embodiment, a nucleic acid such as DNA is extracted from a nucleated blood sample, particularly an avian blood sample, by placing the sample in a microtiter well, lysing the cells to release the DNA, precipitating the nucleic acid within the well of the microtiter plate such that the nucleic acid is attached to the well, removing any extraneous material from the well by washing, and subjecting the isolated nucleic acid to an assay.

The present invention further provides a sequence tag for use in a high throughput assay to permit detection of the desired genetic sequence at low copy numbers. For example, in one embodiment, the sequence tag is used in the high throughput assay of the present invention to allow a plasmid to be detected at a level of from about 5 to about 50 copies in the presence of chicken genomic DNA.

Also contemplated within the scope of the present invention is a high throughput DNA extraction method adapted for use with blood from species other than avian. For example, an alternate embodiment of the present invention provides a DNA extraction method that uses mammalian red blood cells in the high throughput assay of the present invention. In one aspect of the present invention, mammalian blood is enriched for those RBCs that are nucleated, as with cell sorting, centrifugation, or the administration of a hemopoietic agent, such that a sufficient amount of nucleated cells can be transferred to each well of a microtiter plate in a volume of 250 μl or less.

In yet another embodiment of the present invention, DNA or other nucleic acid is extracted from nucleated cells other than red blood cells. For example, white blood cells, including granulocytes, neutrophils and mast cells, can be used in the high throughput assay of the present invention.

The present invention may be better understood with reference to the accompanying Examples, which Examples are provided for the purpose of illustration and should not be construed to limit the scope of the invention, which is defined in the claims appended hereto.

EXAMPLE 1
DNA Extraction Method

Briefly, the protocol for DNA extraction from avian blood according to the present invention is as follows:

A. To pre-chilled 96 well-flat bottom polystyrene tissue culture plates, 0.2 ml (can go as high as 0.25 ml) of lysis buffer LB1 (containing 0.32 M sucrose, 10 mM Tris-Cl, 5 mM MgC12, and 1% Triton X-100, at pH 7.5) was added to each well. Duplicate plates were set up for each set of 96 chicks. The 96-well plates were kept on ice until step C below.

B. One to 10 day old White leghorn chicks were heated under a heat lamp to facilitate bleeding, and a heparinized 0.05 ml capillary tube (Fisher, Pittsburgh, Pa.) was filled half-full by pricking a leg vein. Over-filling the capillary tube will allow too much blood to go into the first 96-well plate. Upon filling the capillary tube, one drop (about 8 microliter or $\frac{1}{4}^{th}$ of the capillary) of blood was transferred into one well and its duplicate, each containing LB1. Following transfer, the blood and LB1 were mixed in each well using the capillary tube. If chicks older than 10 days are used as blood donors, a 25 G needle and 1 cc syringe primed with 0.05 ml of heparin can be used to collect blood. Transfer one drop (about 8 $\mu$l) into each well.

Note that the lysis solution can hold only so much blood, otherwise the quality of the DNA will significantly decrease. Add enough blood such that the lysis solution is light to medium red. If significant clotting occurs, the cell pellet is lost during subsequent steps, or the DNA appears yellow or brown after resuspension, it is likely that too much blood was added to LB1.

C. Each microtiter plate was centrifuged at about 960 g (about 2000 rpm in a tabletop centrifuge) for 7 minutes to pellet nuclei.

D. The supernatent was carefully aspirated from each well, leaving a layer of nuclei remaining at the bottom of each microtiter well. Most of the red color was gone.

E. 0.05 ml of lysis buffer 2 (LB2 containing 10 mM Tris-Cl, 10 mM NaCl, 10 mM EDTA, and 1 mg/ml proteinase K at pH 8.0) was added to each well, and the plates incubated for 2 hours at 56–65° C.

F. To each well, 1.5 $\mu$l M NaCl and 0.01 ml cold ethanol (premixed) was added, without mixing, and the plates were left overnight at 4° C.

G. The supernatant was then removed by carefully inverting the plate and pouring the supernatant into a large beaker.

H. The pellet was washed 3–4 times with 70% ethanol, using about 0.2 ml per well. The supernatant was removed by carefully inverting the plate and, following the last wash, the plate was blotted onto a paper towel.

I. Wells which lost their DNA were marked by holding up the plates against a black background and marking wells which had no dense white mat on the bottom of the well.

J. The DNA samples were air-dried completely (as indicated by complete transparency of the DNA) by incubating the plates at 65° C. for one hour.

K. 0.2 ml PCR or DNA grade water was added to each well, a sheet of Parafilm was placed over the wells, and a lid tightly placed on top of the parafilm. The DNA samples were allowed to resuspend overnight at 4° C. The next day each plate was gently shaken at the lowest speed on a vortexer with a microplate holder at room temperature for 6–8 hours or overnight. The resulting DNA solution appeared completely clear.

Referring now to FIG. 1, a schematic is provided to illustrate the steps of the DNA extraction method according to the present invention. As illustrated in the schematic, 8 to 12 $\mu$l of avian blood is added to lysis buffer 1 (LB1) in each well of a 96-well plate. After lysis of the red blood cell plasma membrane occurs, the nuclei are spun down and the supernatents containing cytoplasmic proteins are removed. A proteinase K solution is added such that the bed of nuclei is not disturbed. After lysis of the nuclei, a solution of ethanol and NaCl is gently added. The chromosomal DNA precipitates and forms a dense white mat which adheres tightly to the bottom of the well. The DNA mat can be easily washed with 70% ethanol several times without centrifugation. The solutions are simply poured off by hand between each wash. After the last wash, the plate is inverted onto some paper towels, dried and water is added to each well to resuspend the DNA.

If the DNA extracted according to the present invention is to be used in a qualitative assay, the amount of DNA present in each well does not need to be quantitated. Rather, after the last 70% ethanol wash and before drying, a visual inspection of the plate will indicate which wells do not have an adequate amount of DNA. A well containing an adequate amount of DNA will have a dense white mat of DNA at its bottom, which is easily visualized if the plate is held up against a black background.

EXAMPLE 2

Average DNA Yield Using High Throughput DNA Extraction

Three separate DNA extraction experiments were conducted using blood samples obtained from White Leghorn chickens as described in Example 1 above. To quantify yield following high throughput extraction, 2 ul of DNA was added to 5 ul of Picogreen (Molecular Probes, Eugene, Oreg.) in 1.0 ml of TE buffer (containing 0.1 M Tris-base, and 0.005 M EDTA at pH 7.5). Samples were read on a Turner Designs TD-700 Fluorometer using CsCl-banded plasmid DNA quanitated by absorbance at $A_{260}$ as a standard Results of these experiments showed that 1 $\mu$l of DNA extracted and resuspended according to the high throughput method of the present invention typically contained 100 to 600 ng of genomic DNA. The average DNA yield was approximately 340 ng/$\mu$l±120 ng/$\mu$l, as summarized in the following table:

| Yield using High Througput DNA Extraction from Chicken Red Blood Cells | | | |
| --- | --- | --- | --- |
| Experiment | Average (ng/$\mu$l) | Standard deviation | Number of samples |
| 1 | 362.5 | 116.0 | 23 |
| 2 | 357.8 | 149.1 | 8 |
| 3 | 313.9 | 120.7 | 8 |

Figure 2:
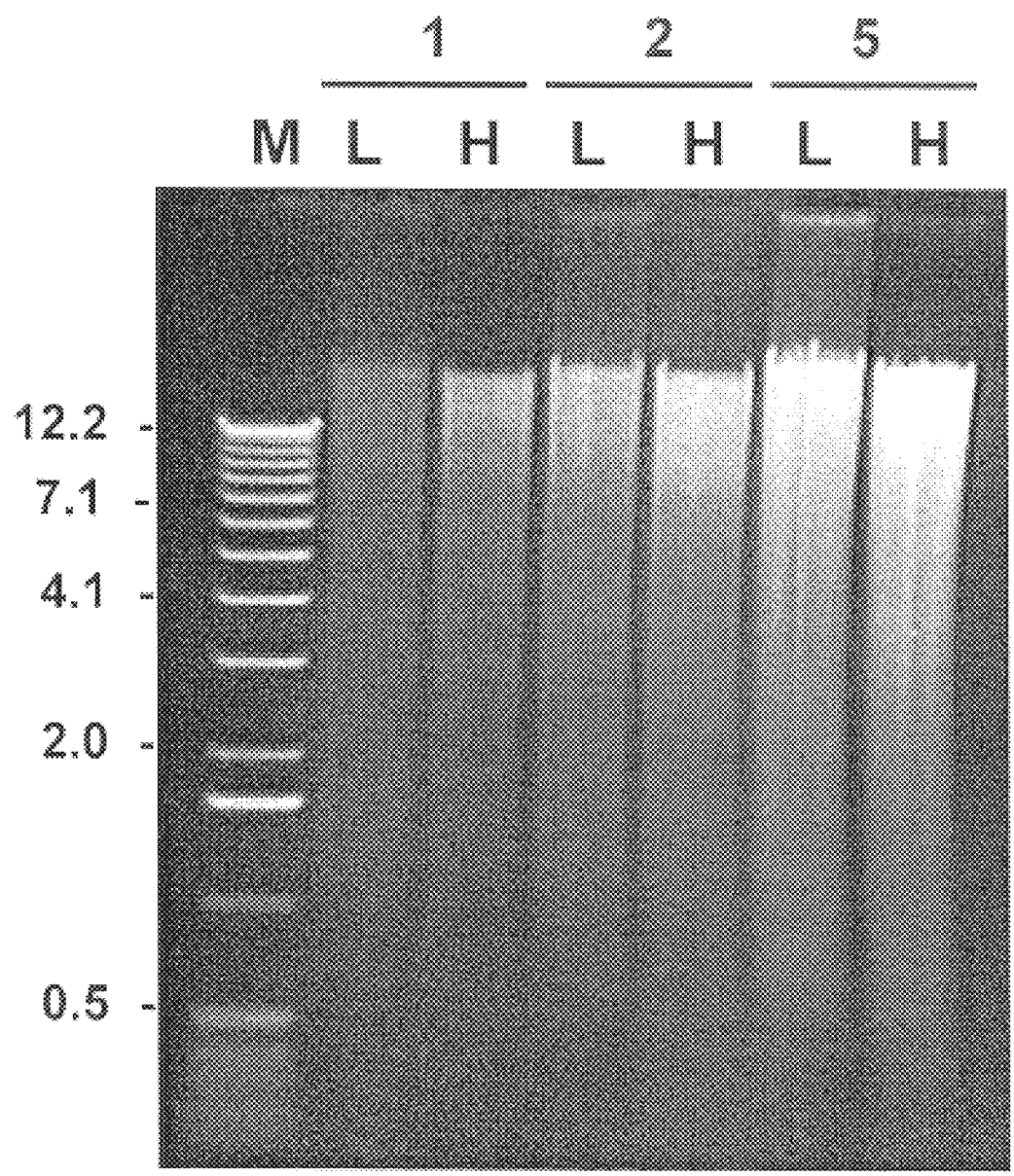
FIG. 2 is a photograph of an agarose gel. DNA was extracted from blood obtained from White Leghorn chickens using either a conventional phenol-based method or the method of the present invention. After extraction, DNA samples were quantitated by absorbance at 260 nanometers and 1, 2 and 5 $\mu$g of each sample was separated on a 0.8% agarose gel. Samples extracted using the phenol-based method are shown in lanes marked as L, while lanes marked as H contain DNA samples extracted according to the method of the present invention. Lane M contains a DNA standard with molecular sizes indicated as kilobase pairs.

Referring now to FIG. 2, a photograph of an agarose gel is presented which compares DNA extracted according to the method of the present invention with that obtained using a conventional phenol-based method (see, for example, the standard phenol extraction protocol provided in "*Molecular Cloning: A Laboratory Manual,*" 2nd ed., J. Sambrook et al., eds., Cold Spring Harbor Press, 1989 and *Methods in Plant Molecular Biology: A Laboratory Course Manual,* P. Maliga et al., eds., Cold Spring Harbor Press, 1994).

Blood obtained from White Leghorn chickens was extracted according to either the high throughput method of the present invention, as described in Example 1, or a conventional phenol based method. After extraction, DNA samples were quantitated by absorbance at 260 nanometers, loaded onto an 0.8% agarose gel (at 1, 2 and 5 $\mu$g concentrations of DNA) and subjected to electrophoresis using a conventional protocol. The gel was visualized using an ethidium bromide stain to compare the quality of the DNA extracted according to the present invention (lanes marked as H) with that extracted using a conventional phenol-based technique (lanes marked as L). Lane M contains a DNA standard with molecular sizes indicated. As can be seen in FIG. 2, the quality of the DNA extracted using the high throughput method of the present invention is comparable to that extracted with the conventional technique.

EXAMPLE 3
Identification of a GPDH Transgene in the Chicken Genome Using the High Throughput Assay To demonstrate the compatibility of DNA extracted according to the present invention, two different TAQMAN assays were performed. First, a primer/probe set complementary to the chicken glyceraldehyde-3-phosphate dehydrogenase (GAPDH) was designed and made commercially. The primers were made at Gibco BRL (Gaithersburg, Md.) and the probe was synthesized by Operon Technologies (Alameda, Calif.). The primers used were designed as follows:

chGAPDH-1: 5'-TCCCAGATTTGGCCGTA
TTG-3' (SEQ ID NO: 1)

and chGAPDH-2: 5'-CCACTTGGACTTTGCC
AGAGA-3' (SEQ ID NO: 2).

The sequence of the chGAPDH probe was 5'-CCGCCTGGTCACCAGGGCTG-3' (SEQ ID NO: 3). The chGAPDH probe was labeled with FAM (6-carboxyfluorescin) at the 5' end and TAMRA (N,N,N', N'-tetramethyl-6-carboxyrhodamine) at the 3' end. The TAQMAN assay measures the increase of relative fluorescence due to hybridization of the chGPDH probe to the PCR product and the resulting endonucleolytic cleavage of the probe. The cleavage releases the FAM molecule from the probe so that its fluorescence is no longer quenched by TAMRA.

TAQMAN reactions were carried out in 50 ul volumes by adding 100 to 300 ng of DNA, extracted from blood obtained from randomly-selected White Leghorn chicks according to the method of the present invention described in Example 1 above. To each reaction tube, 0.75×PCR Buffer (Perkin-Elmer, Foster City, Calif.), 0.25×TAQMAN buffer (Perkin-Elmer), 2.5 mM MgC12, 5% DMSO, 125 $\mu$M dATP, 125 $\mu$M dCTP, 125 $\mu$M dGTP, 250 $\mu$M UTP, 0.9 $\mu$M forward primer, 0.9 $\mu$M reverse primer, 40 nM chGAPDH probe, 0.05 U/$\mu$l AmpliTaq Gold DNA Polymerase (Perkin-Elmer), 0.004 U/$\mu$l and AmpErase UNG (Perkin-Elmer) was added according to the manufacturer's recommendations. Reactions were analyzed on a Perkin-Elmer Applied Biosystems Sequence Detector Model 7700 using the following conditions: 50° C. for 2 minutes, 950° C. for 10 minutes, followed by 40 or 50 cycles of 95° C. for 15 seconds and 60° C. for 1 minute.

Results of the TAQMAN reaction were visualized as an increase in the fluorescence ($\epsilon$Rn) during each cycle of the PCR reaction. An increase in $\epsilon$Rn at an earlier cycle indicates the presence of more copies of that particular sequence, whereas an increase in $\epsilon$Rn at a later cycle indicates that fewer copies of the sequence are present. Thus, TAQMAN data can determine the presence of a specific sequence and the relative quantity of that sequence.

Figure 3:
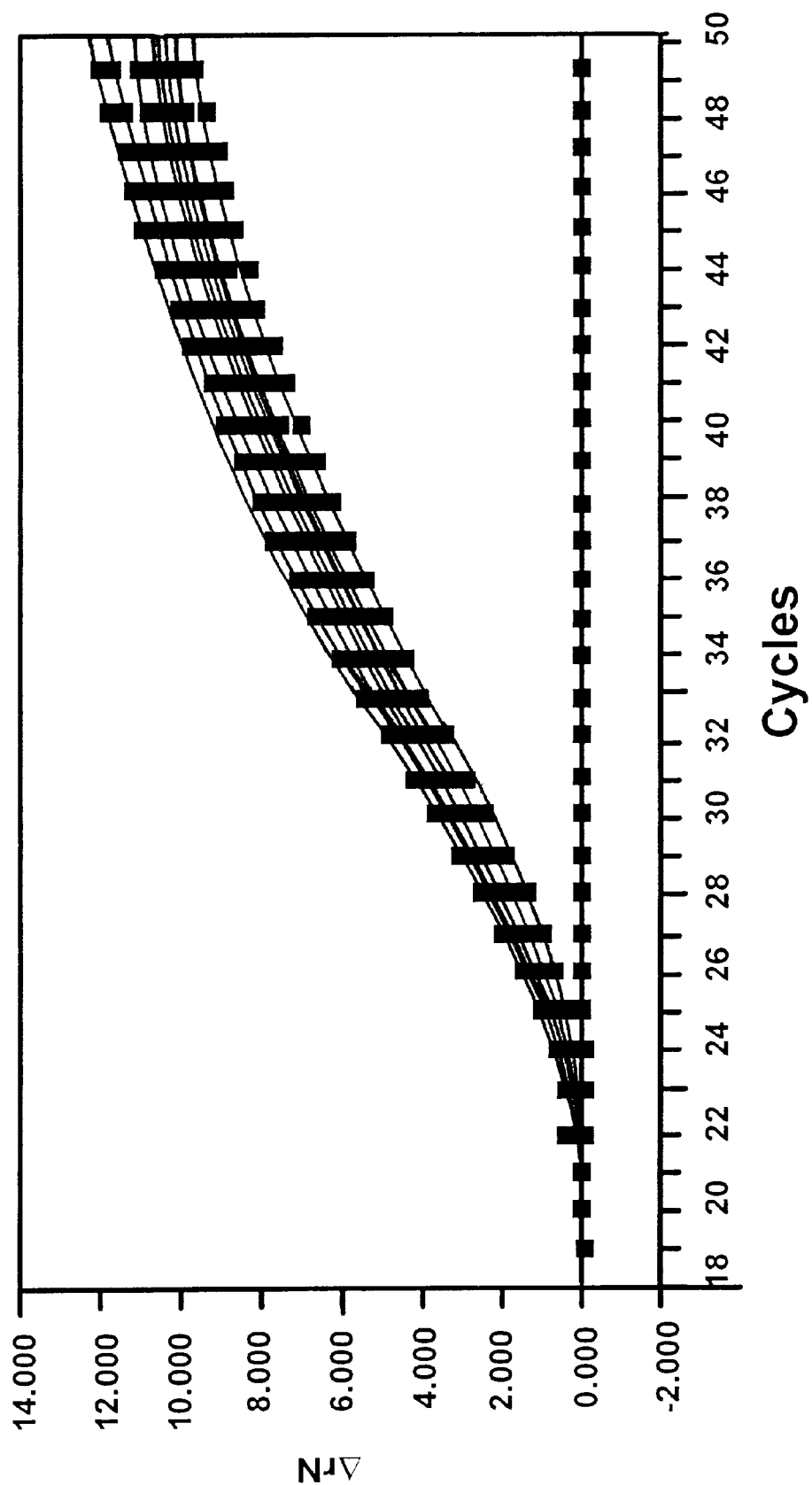
FIG. 3 is a graph illustrating results of an experiment performed as described in Example 3, using the high throughput DNA extraction method of the present invention with an assay to detect the insertion of the chicken glyceraldehyde-3-phosphate dehydrogenase (GAPDH) gene. Primers and a FAM/TAMRA-modified oligonucleotide probe complementary to the chicken GAPDH gene was used in a TAQMAN reaction to confirm the reliability of the high throughput DNA extraction method.

FIG. 3 depicts the results of the TAQMAN amplification assay measuring fluorescence at each cycle of the PCR reaction. The cycle number is shown on the x-axis (only cycles 18–50 are shown). $\Delta$Rn is the increase of relative fluorescence due to hybridization of the chGAPDH probe to the PCR product and the resulting endonucleolytic cleavage of the probe. As shown in FIG. 3, the three control samples (blanks) produced overlapping curves that show no increase in $\Delta$Rn, while the DNA samples obtained from all 21 White Leghorn chicks gave rise to very similar amplification plots showing hybridization of the probe to the chGAPDH gene. These results indicate that the high throughput DNA extraction method of the present invention used with TAQMAN amplification assay provides an accurate and consistent method to detect the presence of a specific gene sequence in genomic DNA.

EXAMPLE 4
Construction of a Sequence Tag for Use in a High Throughput Genetic Sequence Method A significant hurdle in the design of targeting vectors is the inability to detect plasmids that mimic a targeted gene using PCR. We found that, under a variety of conditions, the limit of detection of test plasmids was 5000 copies or greater. The main obstacle is that, when nanogram amounts of chicken genomic DNA was added to a PCR reaction, the reactions were significantly inhibited although, in the absence of chicken DNA, detection limits of our assay were 10 to 50 copies. Chicken genomic DNA prepared by several different methods and derived from different breeds of chicken was tried, but all resulted in unacceptable detection limits in the PCR assay, making it impossible to correctly identify targeted cells.

Different primers can be tried to overcome this problem, but this can be a costly and time-consuming process. In certain cases, such as designing primers to detect integration of a targeting vector into its target gene, the sequences from which to choose the primers is limited to specific areas of the targeting vector and the target gene. For instance, the primer specific for the targeting vector should reside within the 3' untranslated region (UTR) of the selection cassette. However, most 3' UTRs are very short, limiting the choice of potential primer binding sites. In addition, the primer binding site should reside relatively close to the 3' end of the 3' UTR to keep the length of the PCR product as short as possible. The longer the PCR product, the more inefficient the PCR reaction.

In an attempt to improve the limits of detection in the presence of chicken genomic DNA, a sequence tag, NeoRev1 (SEQ ID NO.: 6) was constructed as is described in more detail below. Results using the sequence tag with a template in the high throughput assay of the present invention show that the template can be detected in extremely low copy numbers (5–20 copies) even in the presence of genomic DNA (100 ng of chicken DNA). The NeoRev1 sequence tag can be used in combination with almost any primer that anneals to a site downstream of NeoRev1 and primes DNA synthesis in the opposite direction.

A 62 bp sequence from the Neomycin resistance gene, having the sequence GTG CCC AGT CAT AGC CGA ATA GCC TCT CCA CCC AAG CGG CCG GAG AAC CTG CGT GCA ATC CA (SEQ ID NO.: 5), was cloned into the bovine growth hormone 3' untranslated region (UTR) or polyadenylation sequence such that the new sequence resides just downstream of the UTR (see FIG. 6). This positions a binding site for the primer NeoRev1 (SEQ ID NO.: 6) that will prime DNA synthesis away from the UTR using a PCR reaction. The PCR reactions are relatively insensitive to the type of polymerase used or the magnesium concentration, an indication of the robustness of the reaction.

The inserted sequence contains a binding site for a neomycin probe (Neoprobe; SEQ ID NO.: 7) that can be used in a variety of real-time PCR reactions, including TAQMAN (Perkin Elmer), allowing high throughput detection of a gene targeting event. The inserted sequence contains a second primer binding site (NeoFor1; SEQ ID NO.: 4) which primes synthesis in the direction opposite to that of NeoRev1. The combination of these two primers and the probe enables detection of this sequence, regardless of the sequence context, in an efficient and high throughput manner. Because the amplicon is short (62 bp), amplification is highly efficient. This primer set can be used in a quantitative PCR reaction (realtime or gel-based) to accurately determine the copy number of the transgene. This would be useful, for example, if a transgene has integrated randomly because, in many cases of random insertion, multiple copies of the transgene inserts. Thus, one is required to determine the copy number of the transgene. A second example in which copy number must be determined occurs when the animals are bred to be homozygous for the transgene. In this case, desired animals have twice as many copies of the transgene as their parents or hemizygous (single copy) siblings.

Figure 5:
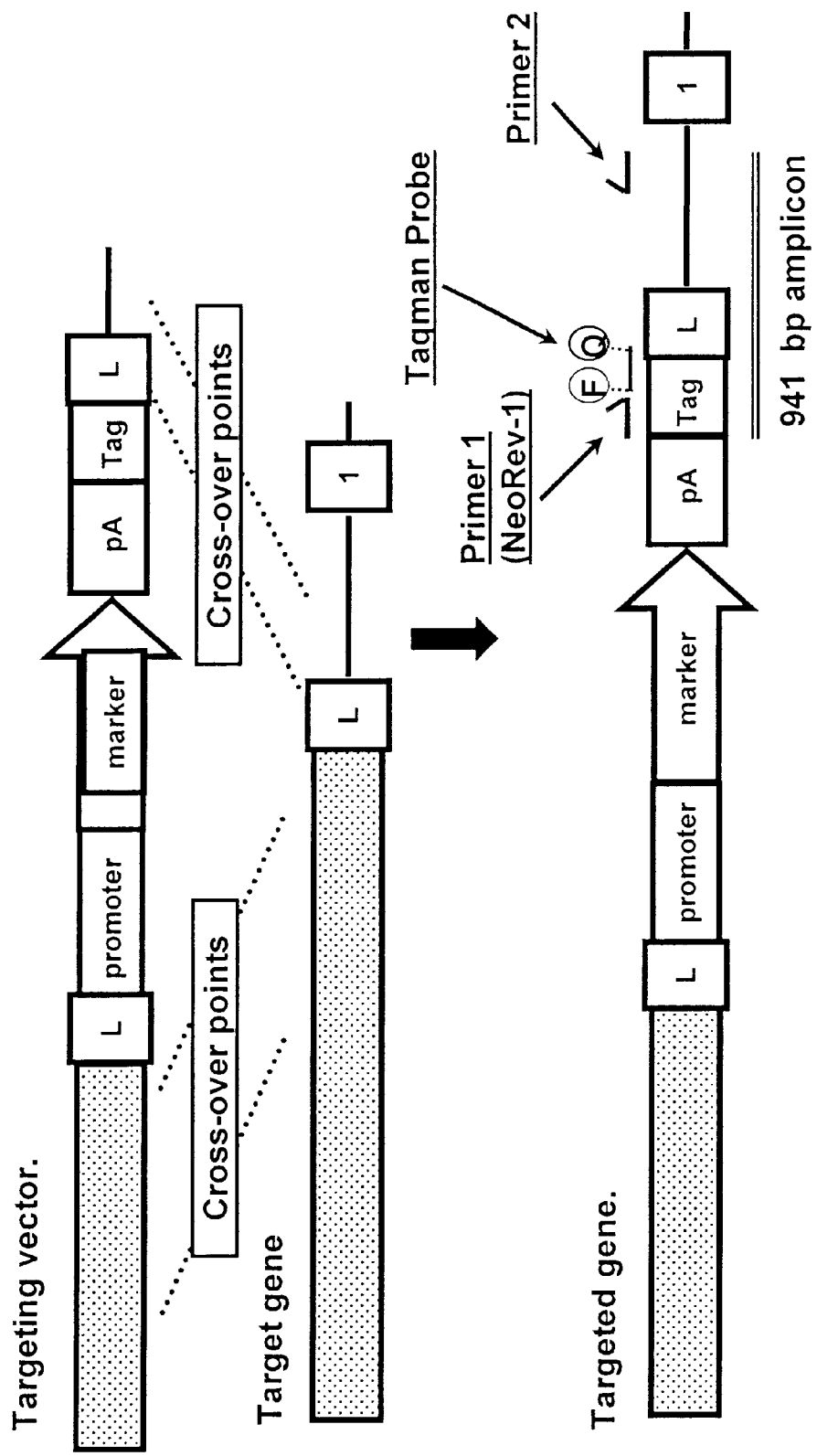
FIG. 5 is a schematic of a targeted gene showing the sequence tag. The targeting vector is modified such that the sequence tag (Tag) is inserted at the 3' end of the polyadenylation signal sequence (pA). Upon introduction of the vector into the desired cells, the vector recombines with the target gene. DNA is extracted from the cells and screened for those with a targeted gene using a PCR assay with primers NeoRev-1 and primer 2. A TAQMAN probe (Neoprobe) can be added to the reaction if a realtime PCR reaction is to be run.

Referring now to FIG. 5, a targeting vector was constructed by subcloning of the 62 bp sequence (SEQ ID NO.: 5) shown in FIG. 6 into a restriction site at the 3' end of the polyadenylation signal. In this particular case, a 62 bp product was produced by PCR by using the neomycin resistance gene (*E.coli* Transposon Tn5) as the template and using the following primers:

NeoFor1: 5'-TGGATTGCACGCAGGTTCT-3' (SEQ ID NO.: 4), and

NeoRev1: 5'-GTGCCCAGTCATAGCCGAAT-3' (SEQ ID NO.: 6).

The primers were kinased with T4 DNA Kinase and ATP prior to PCR. The vector was cut with a restriction site that produced a blunt end and ligated to the PCR product. A subclone was selected in which the PCR product had inserted in the reverse orientation such that the NeoRev1 primer primed DNA synthesis away from the polyadenylation signal, as shown in FIG. 5. For the purposes of this application, this vector is referred to as Targeting Vector-Transgene Tag-rev or TV-TTrev.

To mimic a targeted gene, the 3' flank of the targeting vector, which is homologous to a region of the chicken ovalbumin gene, was replaced by a longer segment of the same region of the gene. This vector is referred to as Targeting Test Vector-Transgene Tag-rev or TTV-TTrev.

A clone in which the PCR product was in the forward orientation was also selected. In this case the NeoFor1 sequence tag primes DNA synthesis away from the polyadenylation signal. The analogous test vector is referred to as Targeting Test Vector-Transgene Tag-for or TTV-TTfor. When this vector is used, the NeoFor1 sequence tag would be used to prime DNA synthesis. Results comparing a high throughput detection assay for TTV-TTfor using the NeoFor1 sequence tag and OV18rev primer (SEQ ID NO.: 8; 5'-CAA TAG AAG ATT TAT ACT TGT TCT GTC TGT TT) with an assay detecting TTV-TTrev with NeoRev1 and OV18rev show the NeoFor1 sequence tag and OV18rev assay has a much lower sensitivity (10–100 fold) than that of the TTV-TTrev and primers NeoRev1 and OV18rev.

The sensitivity of detection using the NeoRev1 sequence tag was tested as follows: TAQMAN reactions were carried out in 20 ul volumes and all reactions had 150 ng of White Leghorn DNA, extracted from blood obtained from randomly-selected chicks according to the method of the present invention described in Example 1 above. To each reaction tube, 0.75×PCR Buffer (Perkin-Elmer, Foster City, Calif.), 0.25×TAQMAN buffer (Perkin-Elmer), 2.5 mM MgC12, 5% DMSO, 125 µM dATP, 125 µM dCTP, 125 µM dGTP, 250 µM UTP (dNTPS and UTP were from Perkin-Elmer), 0.9 µM Neofor-1, 0.9 µM OV18rev, 40 nM Neoprobe, 0.05 U/µl AmpliTaq Gold DNA Polymerase (Applied Biosystems, Foster City, Calif.) and 0.004 U/µl AmpErase UNG (Perkin-Elmer) was added according to the manufacturer's recommendations. In some cases AmpliTaq Gold DNA Polymerase was replaced with Promega Taq DNA polymerase (Promega, Madison, Wis.). Additionally the Perkin-Elmer dNTPs/UTP mixture can be substituted with dNTPs from Roche (catalog number 1969064, Indianapolis, Ind.). Reactions containing AmpliTaq Gold DNA Polymerase were analyzed on a Perkin-Elmer Applied Biosystems Sequence Detector Model 7700 using the following conditions: 50° C. for 2 minutes, 95° C. for 10 minutes, followed by 40 or 50 cycles of 95° C. for 20 seconds and 62.8° C. for 2 minutes, 30 seconds. The following conditions were used when Promega Taq DNA polymerase was in the reaction mixture: 94° C. for 2 minutes, followed by 40 or 50 cycles of 94° C. for 20 seconds and 62.8° C. for 2 minutes, 30 seconds.

Figure 7:
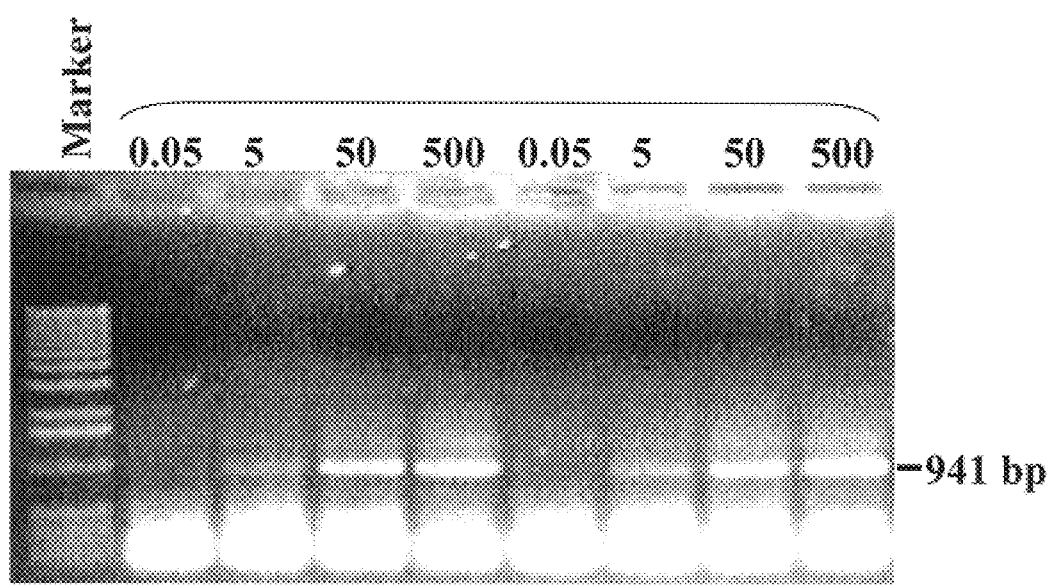
FIG. 7 is an agarose gel showing the results of an experiment using the high throughput assay and sequence tag of the present invention. Results showed detection of the targeted gene at copy number, even in the presence of 150 ng of chicken genomic DNA. Each sample, comprising 10 microliters of a TAQMAN reaction, was run on a 1% agarose gel and stained with ethidium bromide. Lane one is one microgram of one kB DNA Ladder from Gibco-BRL. Plasmid DNA is TTV-TTrev. The number of copies of plasmid in each reaction is indicated above each lane. The desired 941 bp product is indicated.
Figure 8:
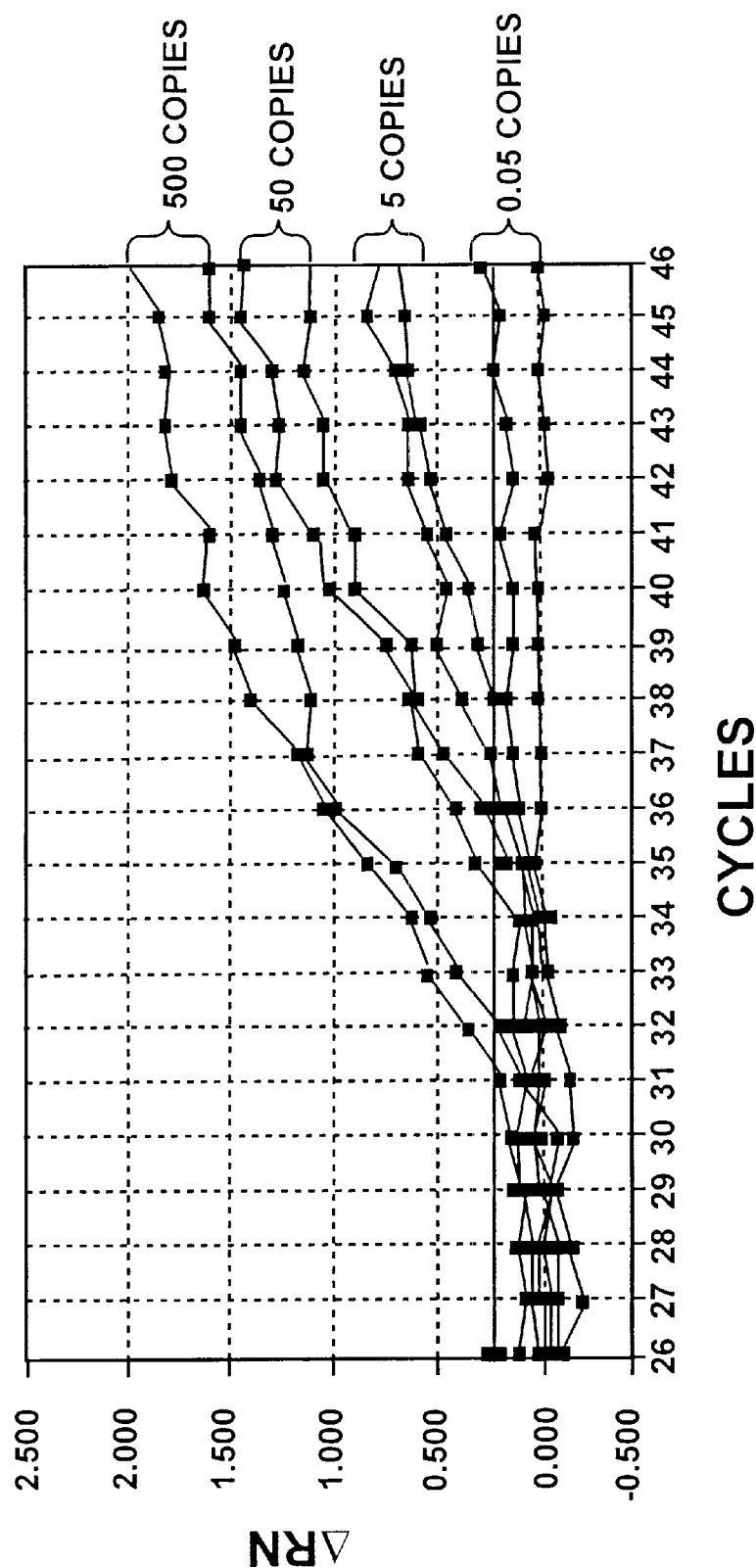
FIG. 8 is a graph depicting real-time PCR detection of a targeted gene using the high throughput assay of the present invention. The reactions were conducted as specified in FIG. 7 above.

FIGS. 7 and 8 show the results of PCR experiments using the NeoRev-1 sequence tag (SEQ ID NO.: 6) as the forward primer and OV18rev (SEQ ID NO.: 8) as .the reverse primer. As can be seen from the agarose gel shown in FIG. 7, the expected 941 bp band is detectable in as low as 5 copies of plasmid DNA. FIG. 8 shows the results from a real-time PCR detection experiment using the sequence tag in the presence of 150 ng of chicken DNA. Results confirm the detection of the desired gene sequence at a 5 copy level.

EXAMPLE 5
Detection of a Neomycin Resistance Gene in the Chicken Genome Using the High Throughput DNA Extraction Method White Leghorn embryos were transduced with a retroviral vector containing the bacterial neomycin resistance gene (NeoR). Because of the inefficiency of transduction, even in the best cases less than 1% of the embryonic cells, including those that give rise to germ tissues, carry a copy of the transgene. Males that arose from the transductions were bred to non-transgenic White Leghorn hens. The resulting chicks were hatched and DNA was extracted in duplicate via the high throughput DNA extraction method described in Example 1 above.

Detection of the neomycin resistance gene was performed using the TAQMAN assay described in Example 3 above, except that the sequence of the primers used was as follows:

NeoFor1: 5'-TGGATTGCACGCAGGTTCT-3' (SEQ ID NO.: 4)

and

NeoRev1: 5'-GTGCCCAGTCATAGCCGMT-3' (SEQ ID NO.: 6).

The sequence of the TAQMAN probe (Neoprobe), designed to be complementary to the bacterial neomycin resistance gene, was 5'-CCTCTCCACCCAAGCGGCCG-3' (SEQ ID NO.: 7). The Neoprobe was labeled with TET (tetrachloro-6-carboxy-fluorescein) or FAM (6-carboxyfluorescin) at the 5' end and TAMRA (N,N,N',N'-tetramethyl-6-carboxyrhodamine) at the 3' end. Reactions were carried out as described in Example 3 above.

Figure 4:
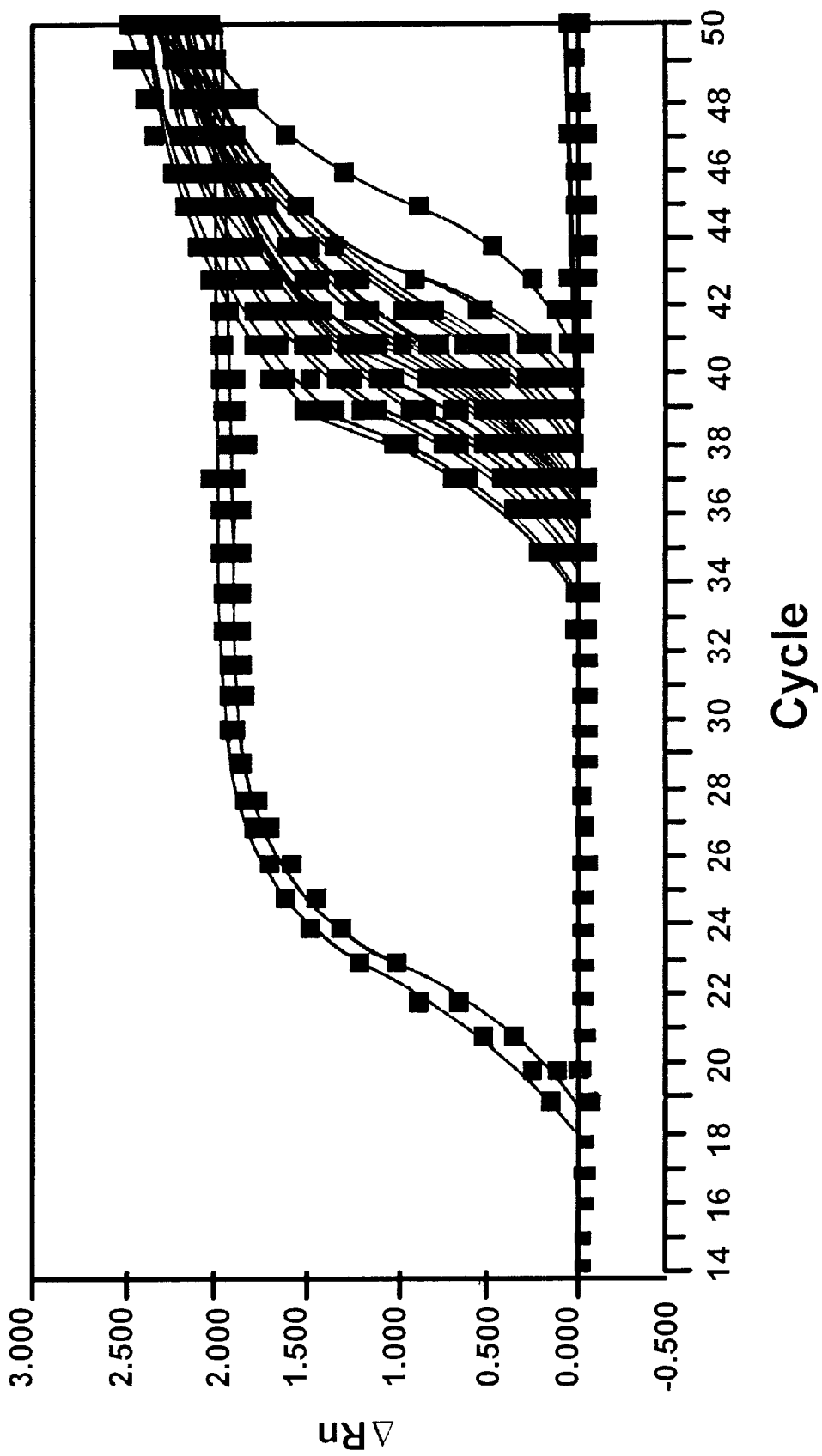
FIG. 4 is a graph illustrating results of an experiment conducting high throughput screening of transgenic offspring according to the present invention. Using the DNA extraction method of the present invention, DNA was extracted from 82 chicks that were bred from a male that was partially transgenic. A TAQMAN reaction with primers and a TET/TAMRA-modified probe complementary to the bacterial neomycin resistance gene was used to detect the presence of the transgene. Curves that did not demonstrate an increase in ΔRn until after cycle 33 indicate that the respective chicks were not transgenic. DNA extracted from a transgenic chick gave rise to amplification at cycle 18. The second curve that began to amplify at cycle 18 was generated by DNA extracted from the same chick on a different 96-well plate.

FIG. 4 shows the results of the neomycin detection assay. As can be seen in FIG. 4, only duplicate DNA samples from a fully transgenic chick demonstrated an increase in εRn at a sufficiently early cycle. The other samples began to amplify after cycle 34 due to destabilization of the probe and not due to detection of a specific sequence.

These results demonstrate the feasibility of using the DNA high throughput extraction method of the present invention with a TAQMAN assay designed to detect the presence of a bacterial neomycin resistance transgene. The results also demonstrate the feasibility of using the high throughput DNA extraction method in conjunction with the TAQMAN sequence detection system to screen large numbers of chicks for a desired transgene.

The method of the present invention has widespread implications for the production of transgenic chickens. Not only can this DNA extraction method be used to facilitate the isolation of founder transgenic chicks, but also the method can be used to facilitate the propogation of those chicks into production flocks. Unless birds that are both homozygous for the desired transgene are mated to each other, only a percentage (50–75%) of offspring from a transgenic founder will carry the transgene, necessitating the screening of thousands of chicks for the desired transgene.

The method of the present invention also provides a significant impact for the screening of genetic markers that are associated with wanted or unwanted traits. Once identified, these traits can be enriched or selected against to produce genetically superior offspring using DNA extracted according to the present invention coupled with a screening assay.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole or in part.

What is claimed is:

1. A method for the isolation of nucleic acid from nucleated red blood cells, comprising the steps of:
   a) obtaining a biological sample containing said nucleated red blood cells;
   b) adding the biological sample to a first lysis buffer to lyse plasma membranes, wherein the first lysis buffer is confined in a container that binds a precipitated nucleic acid;
   c) centrifuging the container to yield a supernatant and a pellet;
   d) removing the supernatant from the pellet in the container;
   e) adding a second lysis buffer to the pellet in the container, after which the pellet is incubated in the second lysis buffer for two hours to release a nucleic acid;
   f) precipitating the nucleic acid in the container with a nucleic acid precipitating solution;
   g) washing the nucleic acid in the container;
   h) drying the nucleic acid in the container; and
   i) dissolving the nucleic acid in the container in a solvent.

2. The method of claim 1, wherein the biological sample is obtained from a mammal, a bird, a reptile, a fish or an amphibian.

3. The method of claim 1, wherein the biological sample is from a bird, a reptile, a fish or an amphibian.

4. The method of claim 1, wherein the biological sample is from a bird.

5. The method of claim 1, wherein the container is polystyrene.

6. The method of claim 1, wherein the biological sample is blood.

7. The method of claim 1, wherein the first lysis buffer comprises between about 0.05M and about 1.0M sucrose, between about 5 mM and about 500 mM Tris-HCl, between about 1 mM and about 50 mM $MgCl_2$ and between about 0.1% w/vol and, about 10% w/vol Triton X-100, and a pH between about 5.0 and about 9.0.

8. The method of claim 1, wherein the first lysis buffer comprises between about 0.2M and about 0.5M sucrose, between about 5 mM and about 50 mM Tris-HCl, between about 1 mM and about 10 mM $MgCl_2$ and between about 0.1% w/vol and about 5% w/vol Triton X-100, and a pH between about 6.0 and about 8.0.

9. The method of claim 1, wherein the first lysis buffer comprises about 0.32M sucrose, about 10 mM Tris-HCl, about 5 mM $MgCl_2$ and about 1% w/vol Triton X-100 and a pH about 7.5.

10. The method of claim 1, wherein the second lysis buffer comprises between about 5 mM and about 100 mM Tris-HCl, between about 1 mM and about 100 mM NaCl, between about 1 mM and about 100 mM EDTA, and a protease, and a pH between about 5.0 and about 9.0.

11. The method of claim 1, wherein the second lysis buffer comprises between about 5 mM and about 50 mM Tris-HCl, between about 1 mM and about 50 mM NaCl, between about 1 mM and about 50 mM EDTA, and a protease, and a pH between about 7.0 and about 9.0.

12. The method of claim 1, wherein the second lysis buffer comprises about 10 mM Tris-HCl, about 10 mM NaCl, about 10 mM EDTA, about 1 mg/ml proteinase K, and a pH about 8.0.

13. The method of claim 1, wherein the container comprises a compartmentalized container.

14. The method of claim 1, wherein the container comprises a multi-well plate.

15. The method of claim 1, wherein the nucleic acid precipitating solution comprises about 0.05 M NaCl and ethanol.

16. A method for the high-throughput isolation of nucleic acid from a bird, comprising the steps of:
   a) obtaining a plurality of blood samples containing nucleated blood cells from a bird;
   b) adding the blood samples of step a) to a first lysis buffer, wherein the first lysis buffer comprises about 0.3M sucrose, about 10 mM Tris-HCl, about 5 mM $MgCl_2$ and about 1% wt/vol Triton X-100, at about pH 7.5, and wherein the first lysis buffer is confined in a compartmentalized polystyrene container, and wherein a blood sample of the plurality of blood samples is isolated in a single compartment of the compartmentalized polystyrene container;
   c) centrifuging the compartmentalized polystyrene container to yield a plurality of supernatants and a plurality of pellets;
   d) removing the supernatants from the pellets in the compartmentalized polystyrene container;
   e) adding a second lysis buffer to the pellets in the compartmentalized polystyrene container, wherein the second lysis buffer comprises about 10 mM Tris-HCl, about 10 mM NaCl, about 10 mM EDTA, about 1 mg/ml proteinase K, at about pH 8.0, after which the pellets are incubated in the second lysis buffer for two hours thereby releasing nucleic acid samples from the pellets;

f) precipitating the nucleic acid samples in the compartmentalized polystyrene container with nucleic acid precipitating solution comprising about 0.05 M NaCl and ethanol;

g) washing the nucleic acid samples in the compartmentalized polystyrene container;

h) drying the nucleic acid samples in the compartmentalized polystyrene container; and i) dissolving the nucleic acid samples in the compartmentalized polystyrene container in a solvent.

* * * * *